US005607969A

United States Patent [19]
Milman et al.

[11] Patent Number: 5,607,969
[45] Date of Patent: Mar. 4, 1997

[54] L-DOPA ETHYL ESTER TO TREAT PARKINSON'S DISEASE

[75] Inventors: Isaac Milman, Maale Adumim; Alexander Veinberg, Rehovot; Daphne Atlas, Neve Granot; Eldad Melamed, Mevasserett Zion, all of Israel

[73] Assignees: Yissum Research Development Company of the Hebrew University of Jerusalem; Teva Pharmaceutical Industries Ltd., Both of Jerusalem, Israel

[21] Appl. No.: 442,888

[22] Filed: May 17, 1995

Related U.S. Application Data

[63] Continuation-in-part of Ser. No. 276,196, Jul. 18, 1994, Pat. No. 5,525,631, which is a continuation of Ser. No. 995,847, Dec. 24, 1992, Pat. No. 5,354,885.

[51] Int. Cl.⁶ .................................................. A61K 31/24
[52] U.S. Cl. ............................................................ 514/538
[58] Field of Search ................................... 514/538, 649

[56] References Cited

U.S. PATENT DOCUMENTS

| | | | |
|---|---|---|---|
| 3,803,120 | 4/1974 | Felix | 530/331 |
| 3,939,253 | 2/1976 | Bodor et al. | 514/547 |
| 3,961,041 | 6/1976 | Nishimura et al. | 424/466 |
| 4,035,507 | 7/1977 | Bodor et al. | 514/533 |
| 4,663,349 | 5/1987 | Repta | 514/535 |
| 4,826,875 | 5/1989 | Chiesi | 514/534 |
| 4,916,151 | 4/1990 | Bey et al. | 514/419 |

FOREIGN PATENT DOCUMENTS 1364505  9/1974  United Kingdom .

OTHER PUBLICATIONS

D.R. Cooper et al., "L–Dopa esters as potential prodrugs; behavioural activity in experimental models of Parkinson's disease"; J. Pharm. Pharmacol.; vol. 39: No.8; pp. 627–635.
Cooper, D.R., et al., *Clin. Neuropharmacol.* (1984) 7:89–98
Fix, J.A., et al., *Pharm. Res.* (1989) 6:501–505.
Juncos, J.L., et al., *Neurology* (1987) 37:1242–1245.
Lai, C.M., et al., *J. Pharm. Sci.* (1973) 62:510–511.
Yoshimasa Tomiuchi, et al. *Bull. Chem. Soc. Jpn.* (Oct. 1992) 65:2599–2603.

*Primary Examiner*—Theodore J. Criares
*Attorney, Agent, or Firm*—John P. White

[57] ABSTRACT

Patients suffering from Parkinson's disease are treated by administering a composition which contains an active ingredient and a pharmaceutically acceptable carrier. The active ingredient comprises L-DOPA ethyl ester in an amount which is at least 97% by weight of the active ingredient and L-DOPA in an amount which is less than 1% by weight of the active ingredient.

22 Claims, No Drawings

L-DOPA ETHYL ESTER TO TREAT PARKINSON'S DISEASE

This is a continuation-in-part of U.S. application Ser. No. 08/276,196, filed Jul.18, 1994, now U.S. Pat. No. 5,525,631, issued Jun. 11, 1996, which is a continuation of U.S. Ser. No. 07/995,847, filed Dec. 24, 1992, now U.S. Pat. No. 5,354,885, issued Oct. 11, 1994.

FIELD OF THE INVENTION

The present invention relates to pharmaceutical preparations for the treatment of patients suffering from Parkinson's disease and related indications comprising a highly purified, stable, non-hygroscopic, crystalline composition of L-DOPA ethyl ester.

BACKGROUND OF THE INVENTION

Typically Parkinsonian patients are routinely treated with a combination of levodopa (L-DOPA) and a DOPA decarboxylase inhibitor such as carbidopa or benserazide. Unfortunately, after an initial period of satisfactory, smooth and stable clinical benefit from L-DOPA therapy lasting on the average 2–5 years, the condition of many patients deteriorates and they develop complex dose-related as well as unpredictable response fluctuations. The causes of the response fluctuations are probably multiple and complex, but pharmacokinetic problems (primarily faulty absorption of L-DOPA) may play a critical role. There is a correlation between the clinical fluctuations and the oscillations of L-DOPA plasma levels. Many of the problems are a result of the unfavorable pharmacokinetic properties of L-DOPA, i.e. very poor solubility, poor bioavailability and short half-life in vivo.

A typical problem commonly seen with these patients is the "on-off" oscillations in which daily motor activity is dominated by remarkable swings between off hours, when they are severely incapacitated, rigid, unable to move, and sometimes to speak or swallow, to on periods where they are responsive to L-DOPA and can, more or less, perform. The current treatments (apomorphine, lisuride) used to treat patients in the off period are unsatisfactory.

Injection of soluble esters of L-DOPA has been proposed as a rescue therapy for patients in the off state or as a therapeutic tool for stabilization of patients with severe motor fluctuations following chronic L-DOPA therapy. The L-DOPA methyl ester has been suggested as a suitable drug for treatment of such patients (U.S. Pat. Nos. 5,017,607; 4,826,875; 4,873,263; 4,663,349; 4,771,073; Juncos, et al., Neurology 37:1742 (1987); and Cooper, et al., J. Pharm. Pharmacol. 39:809 (1987)). However, a metabolic product of L-DOPA methyl ester is methanol which has been shown to be toxic. The release of methanol from methyl esters may not present toxic hazards under conditions of administration of small quantities of parent drug and/or under acute conditions. However, when daily doses could potentially be about 1 gram/day, the theoretical exposure increases to about 4 mg./dl., which is close to the upper permissible limit of occupational exposure. This risk of toxicity becomes more significant when one considers the reduced metabolic clearance rate in the elderly and the reduced hepatic metabolic capability. As the majority of the Parkinsonian patients are elderly, this possible risk of toxicity becomes significant.

A more suitable L-DOPA ester for therapy would be the L-DOPA ethyl ester. However, the current literature indicates that it is not possible to develop the L-DOPA ethyl ester in a form suitable for pharmaceutical use, "In view of the potential toxicity that might arise from methanol formation the ethyl ester would ideally have been most suitable for assessment in humans. However, the ethyl ester could not be crystallized as its hydrochloride salt because of its hygroscopic potential. The methyl ester was therefore developed for use in humans." Stocci, F. et al, Movement Disorders, 2:249–256, (1992); at p. 254.

L-DOPA ethyl ester is described in the literature as the hydrochloride salt. However, it is difficult to isolate as a crystalline salt and therefore was described as an amorphous solid (Fix, et al., Pharm. Research 6(6):501–505 (1989)) which is not suitable for pharmaceutical use. Cooper, et al., Clinical Neuropharmacology 7:89–98 (1984) note that L-DOPA ethyl ester hydrochloride salt is hygroscopic and difficult to crystallize during synthesis. We have also confirmed its hygroscopic nature and unsuitability for pharmaceutical use. Clearly, a pure, stable, non-hygroscopic form of L-DOPA ethyl ester is needed for pharmaceutical purposes.

Salts and esters of L-DOPA, including the L-DOPA ethyl ester, are mentioned in Patent GB 1342286 for the treatment of alopecia. The only disclosure regarding the nature of the L-DOPA ethyl ester is that it can be prepared from L-DOPA by conventional methods. However, as noted above, preparation of L-DOPA ethyl ester by conventional methods yields a product which is not suitable for pharmaceutical use because of its lack of purity, its hygroscopicity, and its lack of stability.

GB Patent No. 1,364,505 and corresponding U.S. Pat. No. 3,803,120, assigned to Hoffman-La Roche, describe the synthesis of L-DOPA ethyl ester hydrochloride salt and free base. This compound synthesized is used as an intermediate in the synthesis of other compounds and is not characterized in the patent specification. In agreement with the literature (Fix, et al., Pharm. Research 6 (6):501–505 (1989)) and Cooper, et al., Clinical Neuropharmacology 7:89–98 (1984)) we have found that the L-DOPA ethyl ester hydrochloride salt synthesized by the methods described in these patents is hygroscopic, not stable, difficult to crystallize, and, as a result, difficult to purify. This material cannot be used for pharmaceutical compositions.

Likewise the L-DOPA ethyl ester free base as prepared in these two patents is impure and not stable and thus also is not suitable for pharmaceutical compositions. At best it can be used as a synthetic intermediate for further chemical synthesis as described in the cited patents.

Two references note the synthesis of racemic ethyl ester. (Ginssberg, et al., Zh. Obshch. Khim. 39:1168–1170 (1969) and Venter, et al., S. Afr. Tydskr. Chem. 31:135–137 (1978)). Neither of these references prepare crystalline L-DOPA ethyl ester in a form suitable for pharmaceutical use and certainly there is no teaching or suggestion of the preparation of crystalline L-DOPA-ethyl ester in a form suitable for pharmaceutical use. Both references prepare the material as an intermediate for the synthesis of other materials of interest.

SUMMARY OF THE INVENTION

This invention provides a composition which comprises a pharmaceutically acceptable carrier and an active ingredient. The active ingredient comprises L-DOPA ethyl ester in an amount which is at least 97%, by weight, of the active ingredient, and L-DOPA in an amount which is less than 1% by weight of such active ingredient.

Also provided by this invention is a process for preparing a composition comprising pharmaceutically acceptable, crystalline, non-hygroscopic L-DOPA ethyl ester as free base in an amount which is at least 97% by weight of the composition and L-DOPA in an amount which is less than 1% by weight of the composition.

This invention further provides a method of treating a patient suffering from Parkinson's disease which comprises administering to a patient a therapeutically effective dose of a composition which comprises a therapeutically effective amount of L-DOPA ethyl ester and a pharmaceutically acceptable carrier.

DETAILED DESCRIPTION OF THE INVENTION

This invention provides a composition which comprises a pharmaceutically acceptable carrier and an active ingredient, such active ingredient comprising L-DOPA ethyl ester in an amount which is at least 97% by weight of such active ingredient and L-DOPA in an amount which is less than 1% by weight of such active ingredient. The composition is further characterized by the fact that the L-DOPA ethyl ester content remains at least 97% by weight of the active ingredient after incubation for 6 months at 40° C. L-DOPA ethyl ester may be present in the composition as a free base.

This invention also provides a pharmaceutical composition comprising a pharmaceutically acceptable carrier and the active ingredient mentioned above with a therapeutically effective concentration of L-DOPA ethyl ester.

For the purposes of this invention "pharmaceutically acceptable carrier" means any of the standard pharmaceutical carriers. Examples of suitable carriers are well known in the art and may include, but are not limited to, any of the standard pharmaceutical carriers. In one embodiment of the invention the pharmaceutically acceptable carrier is an aqueous solution. In another embodiment of the invention the aqueous solution is an acid buffered solution, such acid buffered solution may comprise hydrochloric, sulfuric, tartaric, phosphoric, ascorbic, citric, fumaric, maleic, or acetic acid. In one embodiment of the invention the therapeutically effective concentration of L-DOPA ethyl ester is between about 10 and about 1,000 milligram equivalents of L-DOPA per milliliter. In another embodiment of the invention the therapeutically effective concentration of L-DOPA ethyl ester is between about 50 and about 250 milligram equivalents of L-DOPA per milliliter. The pharmaceutical composition preferably has a pH between about 1.5 and about 5.5.

This invention also provides a pharmaceutical composition comprising a therapeutically effective amount of L-DOPA ethyl ester, an acidic solution as the pharmaceutically acceptable carrier, and an inhibitory amount of a decarboxylase inhibitor, such as carbidopa or benserazide, or of a MAO B inhibitor, such as deprenyl. In one embodiment of the invention the acidic solution may be an acid buffered solution.

Further provided by this invention is a pharmaceutical composition comprising a pharmaceutically acceptable carrier in the form of a nonaqueous solution and a therapeutically effective concentration of L-DOPA ethyl ester. For the purposes of this invention "nonaqueous solution" includes, but is not limited to, oil or any other physiologically compatible solvent.

This invention further provides a pharmaceutical composition comprising a pharmaceutically acceptable carrier and an active ingredient, such active ingredient comprising L-DOPA ethyl ester in an amount which is at least 97% by weight of such active ingredient and L-DOPA in an amount which is less than 1% by weight of such active ingredient, wherein the pharmaceutically acceptable carrier is a solid and L-DOPA ethyl ester is present in a therapeutically effective amount. In one embodiment of the invention, the therapeutically effective amount is between 10 and about 1,000 mg. of L-DOPA. In another embodiment, the therapeutically effective amount is between about 50 and about 250 mg. of L-DOPA. This invention also provides the pharmaceutical composition in solid form additionally comprising an effective inhibitory amount of a MAO B inhibitor, such as deprenyl, or of a decarboxylase inhibitor, such as carbidopa or benserazide.

The L-DOPA ethyl ester composition of this invention may be formulated for oral, sub-lingual, parenteral, rectal, intramuscular, i.v., subcutaneous, intranasal, intraduodenal, or intrajejunal administration. These preparations may be in the form of solutions, suspensions, powders for reconstitution, or tablets. The preparation of these formulations is well known to one skilled in the art.

This invention further provides a process for preparing a composition comprising pharmaceutically acceptable, crystalline, non-hygroscopic L-DOPA ethyl ester as free base in an amount which is at least 97% by weight of the composition and L-DOPA in an amount which is less than 1% by weight of the composition. This process comprises reacting L-DOPA with ethanol in the presence of thionyl chloride or an acid catalyst to yield crude L-DOPA ethyl ester hydrochloride. Any volatiles are then removed from the crude L-DOPA ethyl ester hydro chloride, by vacuum distillation. The residue is then dissolved with water containing a suitable antioxidant and the pH is then adjusted to between 6.0 and 7.0 using a suitable base to yield a solution containing L-DOPA ethyl ester free base. To obtain the free base in the solvent phase, the solution is extracted with a suitable antioxidant. The solvent phase is then concentrated at a temperature lower than 40° C. to form a precipitate. The precipitate is then recrystallized in the presence of a second suitable solvent containing a second suitable antioxidant to yield the composition of pharmaceutically acceptable, crystalline, non-hygroscopic L-DOPA ethyl ester free base. The second suitable solvent and the second suitable antioxidant may be identical to or different than the first solvent and first antioxidant.

In one embodiment of the invention, the acid catalyst used to produce pharmaceutically acceptable, crystalline, non-hygroscopic L-DOPA ethyl ester free base is hydrochloric acid or toluene sulfonic acid. In the preferred embodiment of the invention, L-DOPA reacted with ethanol in the presence of thionyl chloride.

Suitable antioxidants for producing the L-DOPA ethyl ester free base are ascorbic acid, BHT, BHA, sodium sulfite sodium metabisulfite propyl gallate, or vitamin E. Suitable solvents are ethyl acetate, methylene chloride, or toluene. The suitable base may be an organic or inorganic base. However, in the preferred embodiment of the invention, the suitable base is sodium hydroxide or sodium carbonate, or a mixture thereof.

The process for making L-DOPA ethyl ester outlined above provides the active ingredient, i.e. at least 97% by weight of L-DOPA ethyl ester by weight of the active ingredient and less than 1% of L-DOPA by weight, which in turn comprises part of the composition provided by the invention. This active ingredient together with a pharmaceutically acceptable carrier comprise the composition and the pharmaceutical composition provided by this invention.

Finally, this invention provides a method of treating a patient suffering from Parkinson's disease. This method comprises administering to the patient a therapeutically effective dose of the pharmaceutical composition described above. In an embodiment of this method, the patient achieves an "on" phase in less time than when the patient is administered L-DOPA. In another embodiment, the patient achieves an "on" phase of longer duration than when the patient is administered L-DOPA. In specific embodiments, the "on" phase is characterized by a decreasd incapacity, decreased rigidity, or increased ability to move, speak or swallow. "On" and "off" phase are preferably determined according to the UPDRS (Unified Parkinson's Disease Rating Scale) profile.

EXAMPLES

The unit dose of formulations containing the L-DOPA ethyl ester ranges from 10–1000 mg. equivalents of L-DOPA. The preferred unit dose is 50–250 mg. equivalents of L-DOPA.

The pharmaceutical compositions of this invention may additionally contain a MAO-B inhibitor or a decarboxylase inhibitor. The compositions may also contain both a MAO-B inhibitor and a decarboxylase inhibitor. MAO-B inhibitors include deprenyl and lazabemide. Decarboxylase inhibitors include benserazide and carbidopa.

The pharmaceutical compositions of this invention may be used for treating a patient suffering from Parkinson's disease or Parkinson's dementia or patients who benefit from dopamine replacement therapy.

The following examples illustrate the invention in more detail without however limiting it.

EXAMPLE 1

Synthesis of L-DOPA Ethyl Ester

Levodopa (50 g.) was added in portions to a cooled (2–8° C.) solution of 30 ml. thionyl chloride in 250 ml. absolute ethanol. The resulting mixture was heated to 40° C. for 16 hours and then the volatiles were removed in vacuo. The residue was dissolved in 50 ml. of water and diluted with a solution of 20 g. of sodium bicarbonate, 26 g. of sodium sulfate and 50 mg. of ascorbic acid in 400 ml. of water. The pH of the resulting solution was carefully adjusted to pH 7 with 10% aqueous sodium hydroxide and it was extracted with deaerated ethyl acetate containing 0.01% BHT.

The combined ethyl acetate solutions were dried over sodium sulfate and partially concentrated at minimal temperature and allowed to stand for 16 hours. The resulting precipitate was isolated by filtration, washed successively with cold ethyl acetate and hexane. This material was recrystallized from deaerated ethyl acetate containing 0.01% BHT to give the title compound in 88% yield.

Melting point 87–89° C.

Anal. Calculated for $C_{11}H_{15}NO_4$: C, 58.67; H 6.67; N, 6.22.

Found: C, 58.87; H, 6.77; N, 6.19. IR(KBr) 3430 $cm^{-1}$, 3320 $cm^{-1}$, 3285 $cm^{-1}$, 3200 $cm^{-1}$, 1720 $cm^{-1}$, 1600 $cm^{-1}$.

EXAMPLE 2

Synthesis of L-DOPA Ethyl Ester as Described in GB 1,364,505 a) The synthesis was performed exactly as described in Example 11 of GB Patent No. 1,364,505 (F. Hoffman-La Roche & Co., 1974). Following the addition of aqueous sodium bicarbonate as described on page 10 line 92 of the patent, the pH was 8.5. As noted below the L-DOPA ethyl ester obtained was not suitable for pharmaceutical use.

Attempts were made to optimize the procedure described in GB Patent No. 1,364,505 (F. Hollman-La Roche & Co., 1974) as follows:

b) The procedure was repeated as described above except that after the bicarbonate addition the pH was 7.4. This was achieved by changing the amount of bicarbonate added.

c) The procedure was repeated as described above except that after the bicarbonate addition the pH was 7.1. This was achieved by changing the amount of bicarbonate added.

As shown below the product obtained from all these syntheses is an inferior product and not suitable for pharmaceutical use. The synthetic method described in this patent cannot be used for obtaining a pharmaceutically useful product.

EXAMPLE 3

Purity and Stability of L-DOPA Ethyl Ester of the Present Invention and that Synthesized in Example 2

The purity of the material synthesized in Examples 1 and 2 is shown below in Table 1:

TABLE 1

| Compound | Assay | Impurities L-DOPA | Others | Melting Point |
|---|---|---|---|---|
| Example 1 | 101.7% | 0.1% | none | 88°C. |
| Example 2a | 87.0% | 1.6% | 13% | 70° C. |
| Example 2b | 87.9% | 1.3% | 8.4% | 70° C. |
| Example 2c | 95.8% | 0.5% | 3.1% | Not Determined |

The stability and purity of the compounds of Example 1 and Example 2 are shown in Table 2.

TABLE 2

STABILITY OF L-DOPA ESTER PREPARED ACCORDING TO EXAMPLES 1 AND 2 CONDITIONS

| | | 40° C. | | | 25° C. −N2 | | |
|---|---|---|---|---|---|---|---|
| | t = 0 | 1 m | 2 m | 4 m | 1 m | 2 m | 4 m |
| ASSAY | | | | | | | |
| Example 1 | | 98.9 | 99.6 | 99.7 | 98.0 | 99.4 | 99.5 |
| Example 2a | 87% | 82.6 | 80.0 | nd | 83.1 | 84.4 | nd |
| Example 2b | 87.9% | 85.1 | 83.3 | 79.2 | 88.0 | 86.8 | 88.1 |
| Example 2c | 95.8% | 91.7 | 93 | 93 | 94.0 | 93.6 | 94.1 |
| COLOR | | | | | | | |
| Example 1 | | A | B | C | A | B | C |
| Example 2a | | E | E | nd | D | E | nd |
| Example 2b | | D/E | D/E | F | D/E | D/E | D/E |
| Example 2c | | D | D/E | F | D | D/E | F |
| IMPURITIES | | | | | | | |
| Example 1 | | 2.4 | 0.7 | 0.5 | 1.2 | 0.7 | 0.6 |
| Example 2a | | 20.9 | 19.3 | nd | 16.9 | 17.2 | nd |
| Example 2b | | 14.0 | 18.2 | nd | 13.0 | 13.9 | 9.7 |
| Example 2c | | 5.7 | 4.8 | 6.4 | 5.6 | 5.1 | 5.6 |

COLOR CODE:
A = White with gray particles
B = Cream

TABLE 2-continued

STABILITY OF L-DOPA ESTER PREPARED
ACCORDING TO EXAMPLES 1 AND 2 CONDITIONS

|  |  | 40° C. |  |  | 25° C. −N2 |  |
|---|---|---|---|---|---|---|
| t = 0 | 1 m | 2 m | 4 m | 1 m | 2 m | 4 m |

C = White-Yellow
D = Yellow
E = Dark Yellow
F = Gray
nd = not determined

EXAMPLE 4

Attempted Purification of Levodopa Ethyl Ester

Levodopa ethyl ester prepared according to the method of Example 2(c) was recrystallized from ethyl acetate. The resulting material was not pharmaceutically pure:

TABLE 3

|  | Impurities |  |  |
|---|---|---|---|
| Assay | Levodopa | Other | melting point |
| a) 95.5% | 0.3% | >1.3% | Not Determined |
| b) 94.7% | 0.3% | >1.4% | 85° C. |

EXAMPLE 5

Oral Solution of L-DOPA Ethyl Ester

| L-DOPA ethyl ester | 50 mg. |
|---|---|
| HCl to pH = 4.5 | |
| Purified water to 100 ml. | |

Optionally one can add flavorings and sweeteners (such as sorbitol) to this solution. Also one can add non-aqueous vehicles such as glycerin in amounts ranging from 0.01% to 90% of the total volume of the solution.

EXAMPLE 6

Oral Solution of L-DOPA Ethyl Ester and Carbidopa

| L-DOPA ethyl ester | 50.0 mg. |
|---|---|
| Carbidopa | 5.0 mg. |
| Disodium EDTA | 0.5 mg. |
| Sodium Metabisulfite | 5.0 mg. |
| Methylparaben | 1.5 mg. |
| Propylparaben | 0.2 mg. |
| Citric Acid | 5.0 mg. |
| HCl to pH = 2 | |
| Purified water to 100 ml. | |

Optionally one can add flavorings and sweeteners (such as sorbitol) to this solution. Also one can add non-aqueous vehicles such as glycerin in amounts ranging from 0.01% to 90% of the total volume of the solution.

EXAMPLE 7

Oral Solution of L-DOPA Ethyl Ester and Benserazide

| L-DOPA ethyl ester | 50.0 mg. |
|---|---|
| Benserazide | 5.0 mg. |
| Disodium EDTA | 0.5 mg. |
| Sodium Metabisulfite | 5.0 mg. |
| Methylparaben | 1.5 mg. |
| Propylparaben | 0.2 mg. |
| Citric Acid | 5.0 mg. |
| HCl to pH = 4 | |
| Purified water to 100 ml. | |

Optionally one can add flavorings and sweeteners (such as sorbitol) to this solution. Also one can add non-aqueous vehicles such as glycerin in amounts ranging from 0.01% to 90% of the total volume of the solution.

EXAMPLE 8

Oral Solution of L-DOPA Ethyl Ester

| L-DOPA ethyl ester | 50.0 mg. |
|---|---|
| Disodium EDTA | 0.5 mg. |
| sodium metabisulfite | 5.0 mg. |
| methylparaben | 1.5 mg. |
| propylparaben | 0.2 mg. |
| Citric Acid | 5.0 mg. |
| HCl to pH = 4 | |
| Purified water to 100 ml. | |

Optionally one can add flavorings and sweeteners (such as sorbitol) to this solution. Also one can add non-aqueous vehicles such as glycerin in amounts ranging from 0.01% to 90% of the total volume of the solution.

EXAMPLE 9

Tablets Containing L-DOPA Ethyl Ester

| L-DOPA ethyl ester | 250 mg. |
|---|---|
| starch | 16.5 mg. |
| sodium starch glycolate | 36 mg. |
| polyvinyl pyrrolidone | 7.3 mt. |
| microcrystalline cellulose | 44 mg. |
| magnesium stearate | 1.5 mg. |

EXAMPLE 10

Tablets Containing L-DOPA Ethyl Ester and Carbidopa

| L-DOPA ethyl ester | 250 mg. |
|---|---|
| carbidopa | 25 mg. |
| starch | 15.5 mg. |
| sodium starch glycolate | 36 mg. |
| polyvinyl pyrrolindone | 7.3 mg. |
| microcrystalline cellulose | 44 mg. |
| magnesium stearate | 1.5 mg. |

EXAMPLE 11

Tablets Containing L-DOPA Ethyl Ester and Benserazide

| | |
|---|---|
| L-DOPA ethyl ester | 250 mg. |
| Benserazide | 25 mg. |
| starch | 16.5 mg. |
| sodium starch glycolate | 36 mg. |
| polyvinyl pyrrolindone | 7.3 mg. |
| microcrystalline cellulose | 44 mg. |
| magnesium stearate | 1.5 mg. |

EXAMPLE 12

Bio-Availability of L-DOPA Ethyl Ester

Three subgroups of rats, each comprising four males and four females, were injected subcutaneously with 100 mg./kg. L-DOPA equivalents as L-DOPA ethyl ester. The L-DOPA ethyl ester was prepared as described in Example 1 and formulated as described in Example 4. After injection, blood samples were taken from the tail at the times shown below and analyzed for L-DOPA as described in T. Wikberg, J. of Pharmaceutical & Biomedical Analysis 9: 167–176 (1991). No L-DOPA ethyl ester was detected in any of the plasma samples. The L-DOPA plasma profile following injection is shown below:

TABLE 4

| Time (min.) | Mean Plasma L-DOPA Levels (μg./ml.) |
|---|---|
| 0 | 0.3 ± 0.06 |
| 10 | 5.0 ± 2.7 |
| 20 | 8.3 ± 0.7 |
| 30 | 8.6 ± 1.3 |
| 60 | 4.1 ± 0.5 |
| 90 | 2.5 ± 0.4 |
| 120 | 1.8 ± 0.4 |
| 180 | 0.8 ± 0.2 |
| 240 | 0.5 ± 0.2 |

This demonstrates that L-DOPA ethyl ester injected subcutaneously is fully converted to L-DOPA with a kinetic profile similar to L-DOPA, but with the advantage of ease of injection. By way of comparison, injection of an equivalent amount of L-DOPA would require an approximately 100-fold larger volume of injection.

EXAMPLE 13

Oral Administration of L-DOPA Ethyl Ester to Volunteers

Human volunteers orally received 100 mg equivalents of L-DOPA as L-DOPA ethyl ester prepared according to Example 1 and formulated as described in Example 5. Plasma levels of L-DOPA following administration of representative patients are listed below in Table 5. This data demonstrates the rapid conversion of L-DOPA ethyl ester to L-DOPA in humans.

TABLE 5

| | PLASMA L-DOPA LEVELS (μg./ml.) | | |
|---|---|---|---|
| Time (min.) | Patient 1 | Patient 2 | Patient 3 |
| 0 | 0.02 | 0.02 | 0.03 |
| 10 | 1.75 | 0.86 | 1.26 |
| 20 | 1.29 | 2.39 | 2.50 |
| 30 | 0.84 | 1.85 | 1.91 |
| 45 | 0.58 | 1.34 | 1.32 |
| 60 | 0.43 | 0.92 | 1.09 |
| 75 | 0.36 | 0.80 | 0.88 |
| 90 | 0.23 | 0.62 | 0.71 |
| 105 | 0.28 | 0.50 | 0.6 |

EXAMPLE 14

Summary of Oral Clinical Trial

A clinical trial was carried out to determine the safety, tolerability, and preliminary efficacy of L-DOPA ethyl ester administered sub-chronically via the oral route in eight fluctuating Parkinsonian patients.

This was the second in a series of oral clinical trials carried out with L-DOPA ethyl ester. The first clinical trial was carried out in five fluctuating Parkinsonian patients in the hospital setting where L-DOPA ethyl ester was administered on four occasions over a two day period. No adverse reactions were recorded in any of the patients from this first clinical trial.

In the second clinical trial, all patients filled out daily diary cards for at least 10 days prior to study entry to ensure their reliability. Upon study entry they were instructed to continue filling out daily diary cards for the 10-day period during which they were taking L-DOPA ethyl ester.

Three out of the patients' normal daily doses with levodopa/carbidopa or levodopa/benserazide were switched to L-DOPA ethyl ester, each day for ten days. At the beginning and end of this ten-day period, a physical exam was performed and blood chemistry analyzed.

The results of this trial demonstrated no patient complaints nor any reported adverse reaction to the ten-day treatment course with L-DOPA ethyl ester. Evaluation of the serum chemistry revealed no abnormalities or changes for any patient following treatment.

The drug, L-DOPA ethyl ester, was well tolerated by all individuals in the trial and analysis of the efficacy data showed a marked beneficial effect of L-DOPA ethyl ester on the latency to initiation of drug action as well as on the duration of the anti-Parkinsonian effect. There was also a significant decrease in the variability of the response of the patient to the drug's effect when dosed with L-DOPA ethyl ester.

The results of this study demonstrate that L-DOPA ethyl ester, administered sub-chronically over a period of ten days, three times per day, to eight Parkinsonian patients was safe, well tolerated, and seems to have a potential advantage when administered to fluctuating patients with unpredictable on/off reactions to their usual therapy by reducing the unpredictability of drug response.

EXAMPLE 15

Summary of Clinical Trial: Administration of L-DOPA Ethyl Ester by Injection

A clinical trial was undertaken to assess the clinical efficacy of L-DOPA ethyl ester administered by sub-cutaneous injection.

Preparation of solution for injection

The solution for injection L-DOPA ethyl ester 100mg, HCl to pH 4.0 and purified water as the vehicle.

Methods

Ten Parkinson's Disease patients having response fluctuations were hospitalized. These patients are typified in have "on" phases fluctuating with incapacitating "off" phases. Patients were administered s.c. or i.m. L-DOPA ethyl ester at escalating doses of 150–300mg in 2ml vehicle, twice daily, one hour after an oral capsule containing 25mg of carbidopa. "Off" and "on" UPDRS (Unified Parkinson's Disease Rating Scale) profiles, time to "on" phase and duration of "on" phase were measured. Blood samples were taken every 10 minutes post-L-DOPA ethyl ester administration for measurement of levodopa levels.

Results

Prior to administration of LDEE the patients typically displayed a mean latency to an "on" phase post-administration of levodopa of 45–75 minutes and a mean duration of "on" phase of approximately 90 minutes. All patients were turned to an "on" phase by s.c. LDEE injection. Table 6 below shows that the latency of onset of "on" phases decreased and duration of "on" phases increased in a dose-dependant manner and corrolated with rapid and sustained plasma levodopa elevations. No local or general side effects were observed.

TABLE 6

| DOSE/ ROUTE OF ADMINI- STRATION | No. OF INJECTIONS | MEAN TIME TO "ON" (RANGE) IN MINUTES | MEAN DURATION OF "ON" (RANGE) IN MINUTES |
|---|---|---|---|
| 75 mg s.c | 1 | — | — |
| 150 mg s.c | 6 | 54 (25–90) | 31.4 (10–55) |
| 150 mg i.m. | 2 | 37.5 (30–45) | 65 (60–70) |
| 200 mg s.c. | 19 | 38.6 (10–120) | 126.9 (10–235) |
| 200 mg i.m. | 5 | 29.2 (20–40) | 104.5 (28–175) |
| 250 mg s.c. | 8 | 27.1 (20–40) | 155 (60–210) |
| 250 mg i.m. | 5 | 27.5 (10–35) | 133.3 (75–170) |
| 300 mg s.c | 6 | 22.8 (5–37) | 193 (80–315) |
| 300 mg i.m. | 7 | 18.3 (5–35) | 196.7 (135–265) |

What is claimed is:

1. A method of treating a patient suffering from Parkinson's disease which comprises administering to the patient a therapeutically effective amount of a composition which comprises:

L-DOPA ethyl ester derived from pharmaceutically acceptable, crystalline, non-hygroscopic L-DOPA ethyl ester of at least ninety-seven percent purity and containing less than one percent by weight L-DOPA, characterized in that the amount of L-DOPA ethyl ester decreases by less than four percent after one month at forty degrees Celsius; and a pharmaceutically acceptable carrier.

2. The method of claim 1, wherein the patient achieves an on phase in less time than when the patient is administered L-DOPA.

3. The method of claim 1, wherein the patient achieves an on phase of longer duration than when the patient is administered L-DOPA.

4. The method of claim 1, wherein the composition is administered subcutaneously.

5. The method of claim 1, wherein the composition is administered intramuscularly.

6. The method of claim 1, wherein the L-DOPA ethyl ester is present as a free base.

7. The method of claim 1, wherein the pharmaceutically acceptable carrier is a solution and the L-DOPA ethyl ester is present at a therapeutically effective concentration.

8. The method of claim 7, wherein the solution is an aqueous solution.

9. The method of claim 8, wherein the aqueous solution is an acidic solution.

10. The method of claim 9, wherein the acidic solution comprises hydrochloric, sulfuric, tartaric, phosphoric, ascorbic, citric, fumaric, maleic, or acetic acid.

11. The method of claim 9, wherein the acidic solution is buffered.

12. The method of claim 9, wherein the pH is between about 1.5 and about 5.5.

13. The method of claim 7, wherein the solution is a nonaqueous solution.

14. The method of claim 7, wherein the therapeutically effective concentration of L-DOPA ethyl ester is between about 10 and about 1,000 milligram equivalents of L-DOPA per milliliter.

15. The method of claim 14, wherein the concentration of L-DOPA ethyl ester is between about 50 and about 250 milligram equivalents of L-DOPA per milliliter.

16. The method of claim 7, further comprising administering an effective inhibitory amount of a monoamine oxidase-B inhibitor.

17. The method of claim 7, further comprising administering an effective inhibitory amount of a decarboxylase inhibitor.

18. The method of claim 1, wherein the pharmaceutically acceptable carrier is a solid and the L-DOPA ethyl ester is present in a therapeutically effective amount.

19. The method of claim 18, wherein the therapeutically effective amount of L-DOPA ethyl ester is between about 10 and about 1,000 milligram equivalents of L-DOPA.

20. The method of claim 18, wherein the amount of L-DOPA ethyl ester is between about 50 and about 250 milligram equivalents of L-DOPA.

21. The method of claim 18, further comprising administering an effective inhibitory amount of monoamine oxidase-B inhibitor.

22. The method of claim 18, further comprising administering an effective inhibitory amount of a decarboxylase inhibitor.

* * * * *